US00PP37791P2

(12) United States Plant Patent
Hansen et al.

(10) Patent No.: US PP37,791 P2
(45) Date of Patent: Oct. 20, 2026

(54) ***AJUGA* PLANT NAMED 'Raspberry Wren'**

(50) Latin Name: *Ajuga reptans*
Varietal Denomination: Raspberry Wren

(71) Applicants: Christopher M. Hansen, Zeeland, MI (US); Curtis J. Andersen, Spring Lake, MI (US); Jacob T. Schimmel, Hudsonville, MI (US)

(72) Inventors: Christopher M. Hansen, Zeeland, MI (US); Curtis J. Andersen, Spring Lake, MI (US); Jacob T. Schimmel, Hudsonville, MI (US)

(73) Assignee: GARDEN SOLUTIONS, LLC, Zeeland, MI (US)

( * ) Notice: Subject to any disclaimer, the term of this patent is extended or adjusted under 35 U.S.C. 154(b) by 0 days.

(21) Appl. No.: 19/372,480

(22) Filed: Oct. 29, 2025

(51) Int. Cl.
*A01H 5/02* (2018.01)
*A01H 6/50* (2018.01)

(52) U.S. Cl.
USPC ..... Plt./401
CPC ..... *A01H 6/50* (2018.05)

(58) Field of Classification Search
USPC ..... Plt./401
CPC ..... A01H 5/02
See application file for complete search history.

(56) References Cited

PUBLICATIONS https://gardensolutionsplants.com/brands/feathered-friends/; 2026; 5 pages.*

* cited by examiner

*Primary Examiner* — Kent L Bell
(74) *Attorney, Agent, or Firm* — Penny J. Aguirre

(57) ABSTRACT

A new cultivar of *Ajuga* plant named 'Raspberry Wren' that is characterized by its yellow to yellow-green foliage that does not burn in full sun, its small leaves, its very floriferous blooming habit, its vigorous growth habit, and its bright pink flowers.

1 Drawing Sheet

Botanical classification: *Ajuga reptans.*
Variety denomination: 'Raspberry Wren'.

BACKGROUND OF THE INVENTION

The present invention relates to a new and distinct cultivar of *Ajuga reptans* and will be referred to hereafter by its cultivar name, 'Raspberry Wren'. 'Raspberry Wren' represents a new cultivar of *Ajuga,* an herbaceous perennial grown for landscape use.

The new Invention arose from an ongoing controlled breeding program in Hudsonville, Michigan. The goal of the breeding program was to develop a new cultivar of *Ajugas* with yellow foliage coloration, bright pink flowers, small leaf size, strong plant vigor and a floriferous, freely blooming habit. The new cultivar arose from a self-pollination of *Ajuga* 'Fanfin' (U.S. Plant Pat. No. 34,650) in February of 2022. 'Raspberry Wren' was selected as a single unique plant from the resulting seedlings of the above cross in April of 2024.

Asexual propagation of the new cultivar was first accomplished by stem tip cuttings under the direction of the Inventors in Hudsonville, Michigan in March of 2023. Asexual propagation by tip stem cuttings has determined that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'Raspberry Wren' as a unique cultivar of *Ajuga.*

1. 'Raspberry Wren' exhibits yellow to yellow-green foliage that does not burn in full sun.
2. 'Raspberry Wren' exhibits small leaves.
3. 'Raspberry Wren' exhibits a very floriferous blooming habit.
4. 'Raspberry Wren' exhibits a vigorous growth habit.
5. 'Raspberry Wren' exhibits bright pink flowers.

The parent plant of 'Raspberry Wren' differs from 'Raspberry Wren' in having leaves that are shorter in length and orange in color and flowers that are blue in color. 'Raspberry Wren' can be most closely compared to *Ajuga reptans* cultivars 'Corcan' (U.S. Plant Pat. No. 34,673) and 'Petpar' (U.S. Plant Pat. No. 34,635). 'Corcan' is similar to 'Raspberry Wren' in having yellow leaves and a similar plant size. 'Corcan' differs from 'Raspberry Wren' in having flowers that are blue in color, fewer flowering stems, and shorter leaves. 'Petpar' is similar to 'Raspberry Wren' in having a similar plant size and leaf size. 'Petpar' differs from 'Raspberry Wren' in having flowers that are blue in color, fewer flowering stems, and leaves that are bronze toned in color.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventors. The Applicants claim a prior art exemption under 35 U.S.C. 102(b)(1) for disclosure and/or sales prior to the filing date but less than one year prior to the effective filing date. Disclosures include but are not limited to website publications by Chris Hansen (Facebook), Garden Solutions Plants, Jeffries Nurseries, and Nursery Management.

BRIEF DESCRIPTION OF THE DRAWING

The accompanying color photograph illustrates the overall appearance and distinct characteristics of an 8-month-old plant of the new *Ajuga* as grown in a greenhouse in a 1-gallon container in Hudsonville, Michigan.

The photograph provides a side view of a plant 'Raspberry Wren' in bloom.

The colors in the photograph may differ slightly from the color values cited in the detailed botanical description, which accurately describe the colors of the new *Ajuga*.

DETAILED BOTANICAL DESCRIPTION

The following is a detailed description of the new cultivar as observed on 8-month-old plants of the new *Ajuga* as grown in 1-gallon containers in a greenhouse in Hudsonville, Michigan. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—6 weeks in late spring in Michigan.

*Plant type.*—Herbaceous perennial.

*Plant habit.*—Dense and rounded, compact upright inflorescences.

*Height and spread.*—27 cm in height (soil level to top of floral plane), an average of 15 cm in height (soil level to top of foliar plane), 20 cm in width (includes runners) as an 8-month-old plant as grown in a container, reaches about 42 cm in width as a 2-year-old plant in the landscape.

*Hardiness.*—At least in U.S.D.A. Zones 4 to 9.

*Diseases and pests.*—High resistance to powdery mildew has been observed (typically caused by *Golovinomyces biocellatus* and *Neoerysiphe galeopsidis*), no susceptibility or resistance to pests has been observed.

*Root description.*—Fine and fibrous, a blend of 158A and NN155A in color.

*Propagation type.*—Stem tip cuttings.

*Root development.*—Time required for root initiation; 10 days, time required to produce a young plant from a rooted cutting; 6 weeks to fully root in a 72-cell plug.

*Growth rate.*—Very vigorous.

*Branching habit.*—Basal rosettes of leaves from rhizomes, produces runners.

Branch description (runners):

*Stolons.*—Quickly spreading growing horizontal to the ground, produces an average of 10 per plant, 5 cm in length, 2 mm in diameter, color; 145A, surface is glossy and glabrous.

Foliage description:

*Leaf shape.*—Spatulate.

*Leaf division.*—Simple.

*Leaf base.*—Truncate.

*Leaf apex.*—Rounded.

*Leaf venation.*—Pinnate veins are slightly sunken on upper surface, colors match leaf colors.

*Leaf margins.*—Entire.

*Leaf attachment and arrangement.*—Whorled, held in clumps.

*Leaf orientation.*—Various angles; horizontal to downward.

*Leaf surface.*—Slightly rugose on upper surface, both surfaces glabrous and glossy.

*Leaf color.*—Young and mature upper and lower surface; varies between 145A, 145C, 145D, and 151A.

*Leaf size.*—Up to 5 cm in length and 4 cm in width.

*Leaf quantity.*—Very dense, an average of 90 leaves per plant inside the dense clump, runners have an average of 4 leaves per runner.

*Leaf attachment.*—Sessile.

Flower description:

*Inflorescence type.*—Verticillaster, terminal spike, individual flowers in clusters held in leaf-axils.

*Inflorescence size.*—An average of 9 cm in height and 3 cm in width.

*Inflorescence number.*—Average of 30.

*Lastingness of inflorescence.*—10 to 14 days, self-cleaning.

*Flower type.*—Labiate.

*Flower number.*—Average of 60 per inflorescence.

*Flower fragrance.*—None.

*Flower buds.*—Oblanceolate in shape, average of 4 mm in length and 2 mm in diameter, color; 150D, immature calyx 150D, surface matte and densely covered with soft woolly pubescence.

*Flower size.*—Average of 9 mm in depth, 5 mm in diameter, throat diameter 2 mm, tube 5 mm in length, 1 mm in diameter.

*Peduncles.*—An average of 8 cm in length and 5 mm in diameter, held vertical, moderately strong, 145C in color, surface is glossy and sparsely covered with very short hairs that match surface color.

*Calyx.*—Rotate and tubular in shape, 2 mm in length and diameter.

*Sepals.*—5, 50% fused at base, average of 1.5 mm in length, 1 mm in width, ovate in shape, apex acute, entire margins, surface is covered with long woolly hairs matching surface color, color inner and outer surface 145A.

*Petals.*—30% of petals fused into tube, central lobe; notched and fused, average of 6 mm in length, 6 mm in width, outer lobes; average of 3 mm in length, 2 mm in width, all lobes; blunt and rounded in shape, obtuse apex, entire margins that are slightly undulated, both surfaces are glabrous, matte and papery texture, color: upper and lower surface when opening and fully open; 92C, lightly flushed at the top with 75A and 75B, as the petals mature turning to; 76D, fading to 85D, flower throat; outer surface covered with woolly soft pubescence, inner surface is smooth and glabrous, color; inner and outer surface when opening and fully open 75B, flower tube; both surfaces glabrous, color inner and outer surface when opening and fully open 92D.

Reproductive organs:

*Pistils*.—1, style; 7 mm in length, NN155D in color, stigma; non-distinguishable, ovary; oblong, 2 mm in length, 1 mm in width, NN155D in color.

*Stamens*.—5, filament; implanted into flower tube, average of 5 mm in length, NN155D in color, anthers; club-shaped, 0.5 mm in diameter, 203A in color, pollen; not observed.

*Fruit/seed*.—Fruit and seed production has not been observed to date.

It is claimed:

1. A new and distinct variety of *Ajuga* plant named 'Raspberry Wren' as described and illustrated herein.

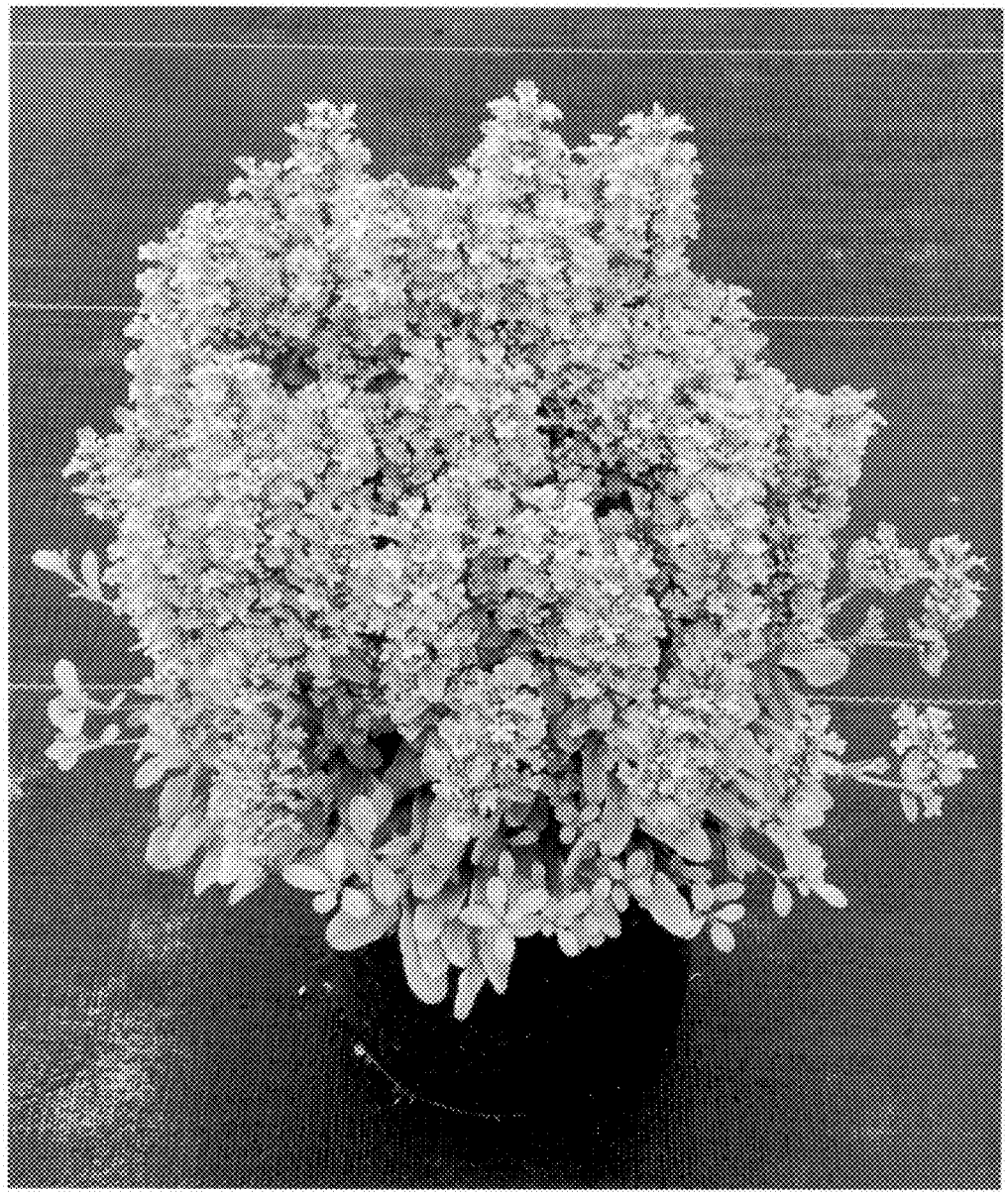

* * * * *